(12) United States Patent
Liu et al.

(10) Patent No.: US 11,124,496 B2
(45) Date of Patent: Sep. 21, 2021

(54) IMIDAZOLIDINE COMPOUNDS

(71) Applicant: Eli Lilly and Company, Indianapolis, IN (US)

(72) Inventors: Lian Zhu Liu, Shanghai (CN); Xiaoqing Wang, Shanghai (CN); Michael Robert Wiley, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/644,746

(22) PCT Filed: Aug. 31, 2018

(86) PCT No.: PCT/US2018/049068
§ 371 (c)(1),
(2) Date: Mar. 5, 2020

(87) PCT Pub. No.: WO2019/050794
PCT Pub. Date: Mar. 14, 2019

(65) Prior Publication Data
US 2021/0061785 A1 Mar. 4, 2021

(30) Foreign Application Priority Data
Sep. 8, 2017 (WO) ................ PCT/CN2017/101042

(51) Int. Cl.
*C07D 401/14* (2006.01)
*A61P 1/16* (2006.01)

(52) U.S. Cl.
CPC .............. *C07D 401/14* (2013.01); *A61P 1/16* (2018.01)

(58) Field of Classification Search
CPC .................................................... C07D 401/14
See application file for complete search history.

(56) References Cited

FOREIGN PATENT DOCUMENTS

| WO | 2013112741 | 8/2013 |
| WO | 2015187499 | 12/2015 |

OTHER PUBLICATIONS

International Search Report of the International Searching Authority pertaining to International Application No. PCT/US2018/049068; dated Nov. 18, 2018; 5 pages.
Written Opinion of the International Searching Authority pertaining to International Application No. PCT/US2018/049068; dated Nov. 18, 2018; 12 pages.

*Primary Examiner* — Brian E McDowell
(74) *Attorney, Agent, or Firm* — Macharri R. Vorndran-Jones

(57) ABSTRACT

The present invention provides a compound of Formula (I) wherein X is selected from the group consisting of $(CH_2)_2$— and $CH_2$—$CH(CH_3)$—; Q is selected from the group consisting of $C(CH_3)_2$ and Formula (a); or a pharmaceutically acceptable salt thereof; compositions, methods to treat liver disease and NASH.

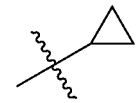

(a)

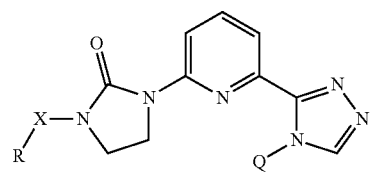

(I)

11 Claims, No Drawings

IMIDAZOLIDINE COMPOUNDS

This invention provides imidazolidine compounds or pharmaceutically acceptable salts thereof, and for use of the compounds in therapy. Imidazolidine compounds of this invention are inhibitors of apoptois signal-regulating kinase 1 (ASK1).

ASK1 is a member of the large mitogen-activated protein kinase kinase kinase ("MAP3K") family. ASK1 activation and signaling are associated with broad range of diseases. Compounds that inhibit ASK1 are desired for use in the treatment of ASK1 mediated conditions.

Compounds that inhibit ASK1 are desired for use in the treatment of Nonalcoholic steatohepatitis (NASH). Nonalcoholic steatohepatitis is a liver disease with an etiological constellation characterized by macrovesicular hepatic steatosis, inflammation hepatocyte ballooning and fibrosis. Currently, there is no approved pharmaceutical medicament specifically for the treatment of nonalcoholic steatohepatitis. There is a need for pharmaceutical medicaments to offer additional treatment options for patients suffering from nonalcoholic steatohepatitis.

U.S. Pat. No. 8,742,126 discloses 5-(4-cyclopropyl-1H-imidazol-1-yl)-N-(6-(4-isopropyl-4H-1,2,4-triazol-3-yl)pyridin-2-yl)-2-fluoro-4-methylbenzamide as an ASK1 inhibitor.

U.S. Patent Application Publication No. US 2015/0342943 discloses a method of preventing and/or treating liver disease using an ASK1 inhibitor.

There is a need for compounds that have ASK1 inhibitory activity.

The present invention provides a compound of Formula I

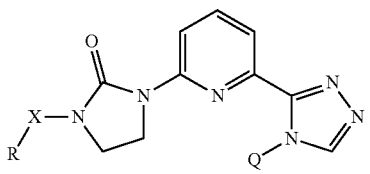

wherein
X is selected from the group consisting of —(CH$_2$)$_2$— and —CH$_2$—CH(CH$_3$)—;
Q is selected from the group consisting of —C(CH$_3$)$_2$ and

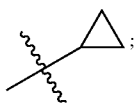 [SMILES: *C1CC1]

R is selected from the group consisting of

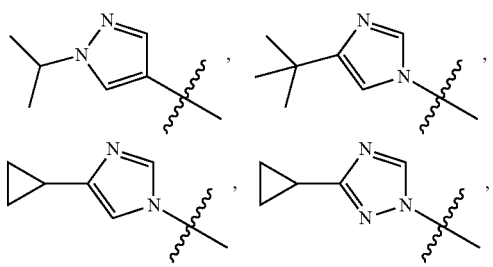

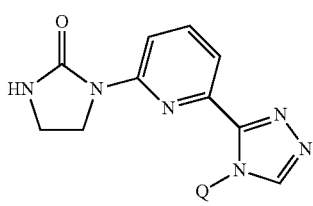

or
a pharmaceutically acceptable salt thereof.
The present invention provides a compound of the Formula II

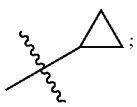

wherein
Q is selected from the group consisting of —C(CH$_3$)$_2$ and

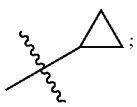 [SMILES: *C1CC1]

or
a pharmaceutically acceptable salt thereof.
In an embodiment, X is —(CH$_2$)$_2$—; Q is —C(CH$_3$)$_2$; and R is selected from the group consisting of

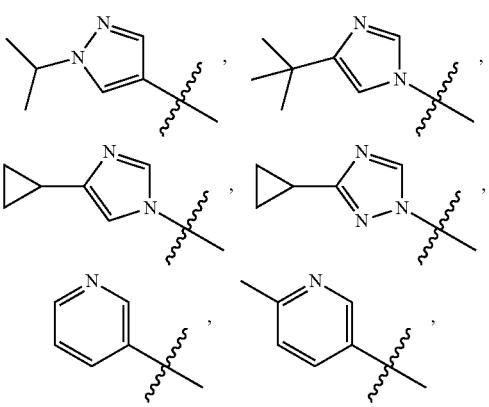

-continued

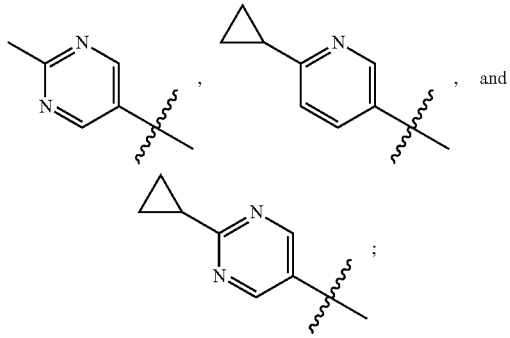

or a pharmaceutically acceptable salt thereof.

In an embodiment, X is —CH2-CH(CH$_3$)—; Q is —C(CH$_3$)$_2$; and R is selected from the group consisting of

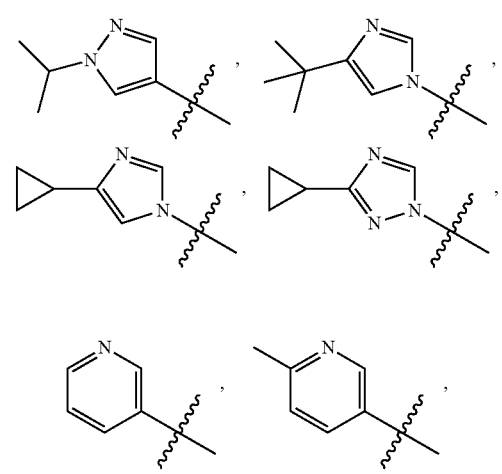

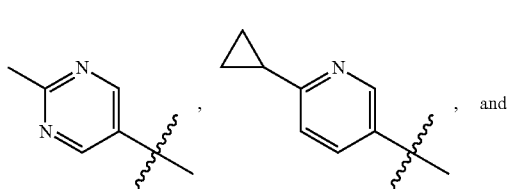

or a pharmaceutically acceptable salt thereof.

In an embodiment, X is —(CH$_2$)$_2$—; Q is

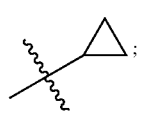

and R is selected from the group consisting of

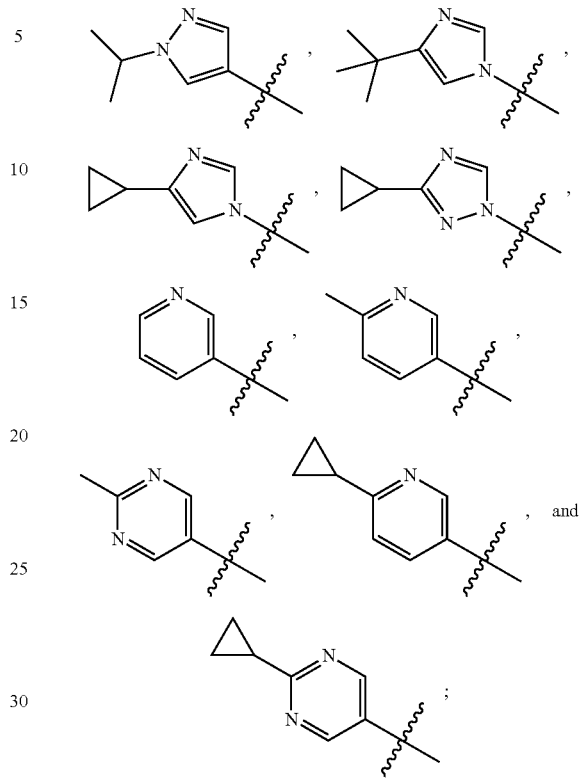

or a pharmaceutically acceptable salt thereof.

In an embodiment, X is —(CH$_2$)$_2$—; Q is —C(CH$_3$)$_2$; and R is selected from the group consisting of

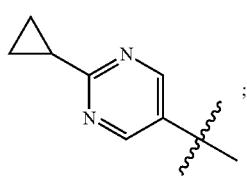

or a pharmaceutically acceptable salt thereof.

In an embodiment, X is —(CH$_2$)$_2$—; Q is —C(CH$_3$)$_2$; and R is selected from the group consisting of

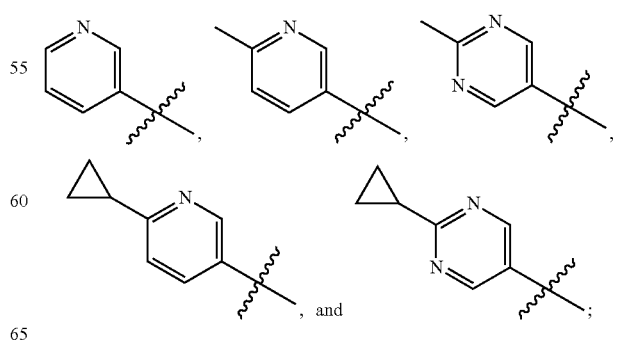

or a pharmaceutically acceptable salt thereof.

In an embodiment, X is —(CH$_2$)$_2$—; Q is —C(CH$_3$)$_2$; and R is selected from the group consisting of

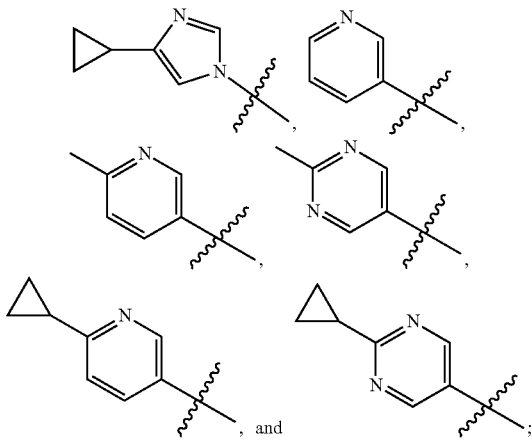

, and or a pharmaceutically acceptable salt thereof.

In an embodiment Q is —C(CH$_3$)$_2$ and R$^2$ is CH$_3$; or a pharmaceutically acceptable salt thereof.

In an embodiment, the compound is 1-(6-(4-isopropyl-4H-1,2,4-triazol-3-yl)pyridin-2-yl)imidazolidin-2-one, or a pharmaceutically acceptable salt thereof.

In an embodiment, 1-(6-(4-isopropyl-4H-1,2,4-triazol-3-yl)pyridin-2-yl)imidazolidin-2-one, or a pharmaceutically acceptable salt thereof is an intermediate useful in the preparation of compounds of Formula I.

In an embodiment, the compound of Formula I is 1-[2-(4-cyclopropylimidazol-1-yl)ethyl]-3-[6-(4-isopropyl-1,2,4-triazol-3-yl)-2-pyridyl]imidazolidin-2-one, or a pharmaceutically acceptable salt thereof.

In an embodiment, the compound of Formula I is 1-[(1R)-2-(4-cyclopropylimidazol-1-yl)-1-methyl-ethyl]-3-[6-(4-isopropyl-1,2,4-triazol-3-yl)-2-pyridyl]imidazolidin-2-one; or a pharmaceutically acceptable salt thereof.

The present invention provides a pharmaceutical composition comprising a compound of Formula I, or a pharmaceutically acceptable salt thereof, together with one or more pharmaceutically acceptable carriers, diluents, or excipients.

The present invention provides a method for treating a condition mediated by ASK1 activity comprising administering to the mammal in need of treatment, an effective amount of a compound of Formula I, or a pharmaceutically acceptable salt thereof. The present invention also provides a method for treating liver disease, comprising administering to a mammal in need thereof, an effective amount of a compound of Formula I, or a pharmaceutically acceptable salt thereof. The present invention provides a method for treating nonalcoholic steatohepatitis (NASH), comprising administering to a mammal in need thereof, an effective amount of a compound of Formula I, or a pharmaceutically acceptable salt thereof.

In another embodiment, the present invention provides a compound of Formula I, or a pharmaceutically acceptable salt thereof, for use in therapy. Further, provided is a compound of the present invention, or a pharmaceutically acceptable salt thereof or pharmaceutical composition, for use in the treatment of liver disease. Further, provided is a compound of the present invention, or a pharmaceutically acceptable salt thereof or pharmaceutical composition, for use in the treatment of NASH.

In another embodiment, provided is a compound of Formula I, or a pharmaceutically acceptable salt thereof, for use in the manufacture of a medicament for the treatment of liver disease. Preferably, the medicament is for the treatment of NASH.

A compound of the present invention is preferably formulated as pharmaceutical compositions administered by any route, which makes the compound bioavailable. Most preferably, such compositions are for oral administration. Such pharmaceutical compositions and processes for preparing same are well known in the art. See, e.g., *Remington: The Science and Practice of Pharmacy* (L. V. Allen, Editor, 22$^{nd}$ Edition, Pharmaceutical Press, 2012).

Compounds of the present invention can be provided as a pharmaceutically acceptable salt. "Pharmaceutically-acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002)

A human is a preferred mammal. As used herein, "patient" refers to a mammal in need of treatment. As used herein, the term "effective amount" or "therapeutically effective amount" of a compound refers to an amount, or a dosage, which is effective in treating a disorder or a disease, such as NASH, chronic kidney disease, or diabetic nephropathy as described herein. The attending diagnostician, as one skilled in the art, can readily determine an effective amount by the use of conventional techniques and by observing results obtained under analogous circumstances. In determining the effective amount or dose of a compound, a number of factors are considered, including but not limited to, the compound to be administered; the co-administration of other agents, if used; the species of mammal; its size, age, and general health; the degree of involvement or the severity of the disorder; the response of the individual patient; the mode of administration; the bioavailability characteristics of the preparation administered; the dose regimen selected; the use of other concomitant medication; and other relevant circumstances.

The pharmaceutical composition is administered to a patient in amounts effective to treat liver disease, more particularly, NASH. An appropriate amount or dose effective to treat a patient can be determined by a health care provider.

The terms "treatment" and "treating" as used herein are intended to refer to all processes wherein there may be a slowing, interrupting, arresting, controlling, or stopping of the progression of an existing disorder and/or symptoms thereof, but does not necessarily indicate a total elimination of all symptoms.

The term "liver disease" as used herein embraces liver conditions or symptoms associated with ASK1 mediation, for example, metabolic liver disease, steatosis, liver fibrosis, primary sclerosing cholangitis (PSC), cirrhosis, liver fibrosis, non-alcoholic fatty liver disease (NAFLD), nonalcoholic steatohepatitis (NASH), hepatic ischemia reperfusion injury, and primary biliary cirrhosis (PBC).

The term "pharmaceutically acceptable carrier, diluent, or excipients" means that the carrier, diluent, and excipients are pharmaceutically compatible with the other ingredients of the composition. In a particular embodiment, the pharmaceutical compositions are formulated as a tablet or capsule for oral administration. The tablet or capsule can include a compound of the present invention in an amount effective to treat liver disease, particularly NASH.

The abbreviations used herein are defined according to *Aldrichimica Acta*, Vol. 17, No. 1, 1984. Other abbreviations are defined as follows: "ACN" refers to acetonitrile; "ADP" refers to adenosine diphosphate; "ATP" refers to adenosine triphosphate; "BSA" refers to Bovine Serum Albumin; "DCM" refers to dichloromethane; "DMEM" refers to Dulbecco's Modified Eagle's Medium; "DMF" refers to dimethylformamide; "DMSO" refers to dimethylsulfoxide; "DTT" refers to dithiothreitol; "EtOAc" refers to ethyl acetate; "FA" refers to formic acid; "FBS" refers to Fetal Bovine Serum; "HEK" refers to human embryonic kidney; "HPLC" refers to high performance liquid chromatography; "$IC_{50}$" refers to the concentration of an agent that produces 50% of the maximal inhibitory response possible for that agent; "MAP" refers to mitogen-activated protein; "MeOH" refers to methanol or methyl alcohol; "MOPS" refers to (3-(N-morpholino)propanesulfonic acid); "pASK1" refers to phosphorylated ASK1; "PE" refers to petroleum ether; "TBAF" refers to tetra-n-butylammonium fluoride; "TFA" refers to trifluoroacetic acid; "THF" refers to tetrahydrofuran; "TIPS" refers to triisopropylsilyl; "$t_{(R)}$" refers to retention time; "XantPhos" refers to 4,5-bis(diphenylphosphino)-9,9-dimethylxanthene. and "Xantphos PD G3" refers to 4,5-bis(diphenylphosphino)-9,9-dimethylxanthene)-2-(2'-amino-1,1'-biphenyl)]palladium(II) methanesulfonate.

The intermediates described in the following preparations may contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, (T. Greene and P. Wuts, eds., 2d ed. 1991).

The compounds of the present invention, or salts thereof, may be prepared by a variety of procedures known in the art, some of which are illustrated in the Preparations and Examples below. The specific synthetic steps for each of the routes described may be combined in different ways, to prepare compounds of the invention, or salts thereof. The products of each step can be recovered by conventional methods well known in the art, including extraction, evaporation, precipitation, chromatography, filtration, trituration, and crystallization. The reagents and starting materials are readily available to one of ordinary skill in the art. Others may be made by standard techniques of organic and heterocyclic chemistry, which are analogous to the syntheses of known structurally similar compounds and the procedures described in the Preparations and Examples, which follow including any novel procedures.

All substituents unless otherwise indicated, are as previously defined. The reagents and starting materials are generally readily available to one of ordinary skill in the art. Others may be made by standard techniques of organic and heterocyclic chemistry, which are analogous to the syntheses of known structurally similar compounds and the procedures described in the Preparations and Examples, which follow including any novel procedures.

PREPARATIONS AND EXAMPLES

Preparation 1

Di-tert-butyl 2-oxoimidazolidine-1,3-dicarboxylate

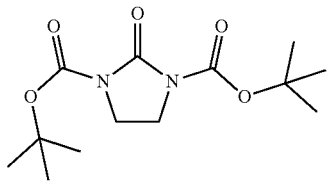 [SMILES: CC(C)(C)OC(=O)N1CCN(C(=O)OC(C)(C)C)C1=O]

Di-tert-butyl dicarbonate (113 g, 511 mmol) and 4-dimethylaminopyridine (0.573 g, 4.65 mmol) is added to a solution of imidazolidin-2-one (20.0 g, 232 mmol) in DMF (100 mL) is added at room temperature (15-20° C.). The reaction mixture is stirred at 70° C. for 16 hours. The reaction mixture is poured into water (600 mL) and filtered. The filter cake is dried to give the title compound (55.0 g, 81.9%) as a white solid. ES/MS (m/z): 231 (M–55).

Preparation 2 tert-Butyl 2-oxoimidazolidine-1-carboxylate

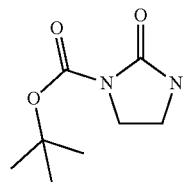

A mixture of di-tert-butyl 2-oxoimidazolidine-1,3-dicarboxylate (55.0 g, 190 mmol) and magnesium perchlorate (8.75 g, 38.0 mmol) in ACN (200 mL) is stirred at 55° C. for 16 hours. The reaction mixture is concentrated under vacuum. Water is added to the residue (300 mL) and the residue is extracted with DCM (3×200 mL). The combined organic extracts are washed with brine (500 mL), dried over sodium sulfate, filtered, and concentrated under reduced pressure. The crude product is purified by silica gel flash chromatography (DCM:MeOH=98:2) to give the title compound (14.0 g, 31.6%) as a yellow oil. ES/MS (m/z): 232 (M+2Na).

Preparation 3 tert-Butyl 3-[6-(4-isopropyl-1,2,4-triazol-3-yl)-2-pyridyl]-2-oxo-imidazolidine-1-carboxylate

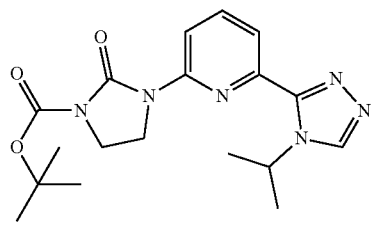 [SMILES: CC(C)n1cnnc1-c1cccc(N2CCN(C(=O)OC(C)(C)C)C2=O)n1]

2-Chloro-6-(4-isopropyl-1,2,4-triazol-3-yl)pyridine (1.0 g, 4.2664 mmol), tert-butyl 2-oxoimidazolidine-1-carboxylate (1.986 g, 8.5328 mmol), Xantphos PD G3 (212.95 mg, 0.21332 mmol), Xantphos (127.2 mg, 0.21332 mmol) and cesium carbonate (4.17 g, 12.799 mmol) are added together in 1,4-dioxane (15 mL) and the resulting mixture is stirred at 110° C. under microwave conditions for 2 hours. The mixture is diluted with DCM, filtered, and concentrated to give the title product (1.672 g, 100%) as a brown solid. ES/MS (m/z): 373 (M+1).

Preparation 4

1-[6-(4-Isopropyl-1,2,4-triazol-3-yl)-2-pyridyl]imidazolidin-2-one

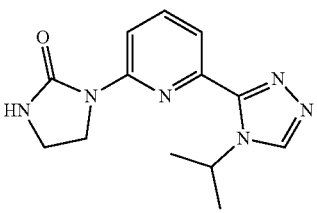 [SMILES: CC(C)n1cnnc1-c1cccc(N2CCNC2=O)n1]

TFA (3 mL, 39.68 mmol) is added to tert-butyl 3-[6-(4-isopropyl-1,2,4-triazol-3-yl)-2-pyridyl]-2-oxo-imidazolidine-1-carboxylate (1.672 g, 4.265 mmol) in DCM (15 mL) at room temperature. The mixture is stirred at room temperature for 4 hours. The mixture is concentrated and purified by silica gel flash chromatography eluting with 4% MeOH in DCM to give the title product (406 mg, 30.76%) as a yellow solid. ES/MS (m/z): 273 (M+1).

Preparation 5

Racemic tert-Butyl N-[2-(4-cyclopropylimidazol-1-yl)-1-methyl-ethyl]carbamate

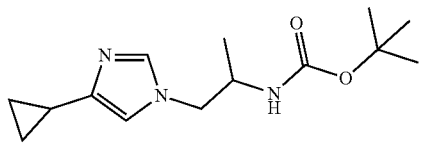 [SMILES: CC(Cn1cnc(C2CC2)c1)NC(=O)OC(C)(C)C]

Preparation 6

Racemic tert-Butyl N-[2-(5-cyclopropylimidazol-1-yl)-1-methyl-ethyl]carbamate

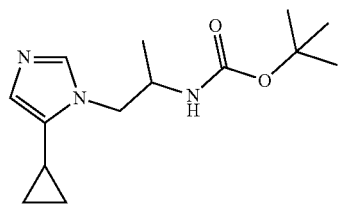 [SMILES: CC(Cn1cncc1C1CC1)NC(=O)OC(C)(C)C]

Potassium hydroxide (73.9 mg, 1.3177 mmol %) and tert-butyl N-[(2R)-2-bromopropyl]carbamate (230.1 mg, 0.96634 mmol) are added to a solution of 4-cyclopropyl-1H-imidazole (100 mg, 0.087849 mmol) in DMSO (2 mL) at 0° C. The mixture is stirred at room temperature for 65 hours. The reaction is quenched with water and extracted with EtOAc (3×). The organic extracts are washed with saturated NaCl (3×), dried over Na$_2$SO$_4$, filtered, and concentrated to dryness. The residue is purified by silica gel flash chromatography with 4% MeOH in DCM to give the title compounds as a mixture of 2 regioisomers (112 mg, 22.82%) and as a yellow oil. ES/MS (m/z): 266 (M+1).

Preparation 7

Racemic-1-(4-cyclopropylimidazol-1-yl)propan-2-amine

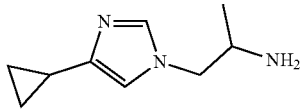

Preparation 8

Racemic-1-(5-cyclopropylimidazol-1-yl)propan-2-amine

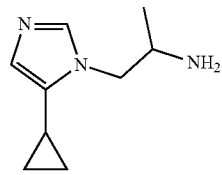

TFA (2 mL, 26.45 mmol) is added to racemic tert-butyl N-[2-(4-cyclopropylimidazol-1-yl)-1-methyl-ethyl]carbamate and to racemic tert-butyl N-[2-(5-cyclopropylimidazol-1-yl)-1-methyl-ethyl]carbamate (112 mg, 0.2005 mmol) in DCM (10 mL) at room temperature. The mixture is stirred at room temperature for 1 hour and is concentrated to give the crude title compounds as a mixture of regioisomers (69.8 mg, 100%) as a yellow oil. ES/MS (m/z): 166 (M+1).

Preparation 9

Racemic tert-Butyl N-[2-[[2-(4-cyclopropylimidazol-1-yl)-1-methyl-ethyl]amino]ethyl]carbamate

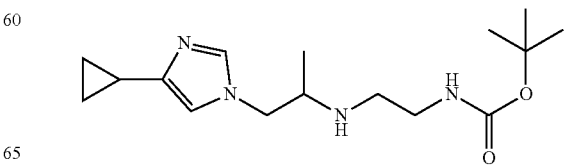

Preparation 10

Racemic tert-Butyl N-[2-[[2-(5-cyclopropylimidazol-1-yl)-1-methyl-ethyl]amino]ethyl]carbamate

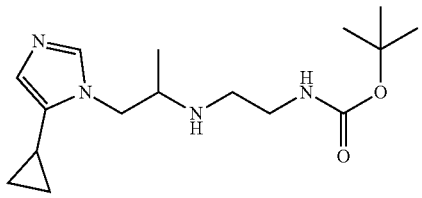 [SMILES: CC(Cn1cncc1C1CC1)NCCNC(=O)OC(C)(C)C]

Sodium triacetoxyborohydride (56.9 mg, 0.260 mmol) is added to a solution of racemic-1-(4-cyclopropylimidazol-1-yl)propan-2-amine and racemic-1-(5-cyclopropylimidazol-1-yl)propan-2-amine (69.7 mg, 0.200 mmol) and tert-butyl N-(2-oxoethyl)carbamate (33.6 mg, 0.200 mmol) in DCM (5 mL) and acetic acid (15.6 mg, 0.260 mmol) at room temperature. The mixture is stirred at room temperature for 18 hours. The reaction is quenched by the addition of saturated NaHCO₃. The mixture is extracted with DCM (3×), the organic extracts are dried over Na₂SO₄, filtered, and concentrated to give the crude title compound as a mixture of regioisomers (130 mg, 100%) as a yellow oil. ES/MS (m/z): 309 (M+1).

Preparation 11

Racemic 1-[2-(4-Cyclopropylimidazol-1-yl)-1-methyl-ethyl]imidazolidin-2-one

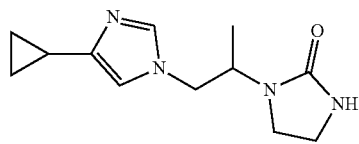 [SMILES: CC(Cn1cnc(C2CC2)c1)N1CCNC1=O]

Preparation 12

Racemic 1-[2-(5-Cyclopropylimidazol-1-yl)-1-methyl-ethyl]imidazolidin-2-one

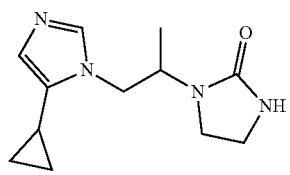 [SMILES: CC(Cn1cncc1C1CC1)N1CCNC1=O]

Potassium tert-butoxide (68.1 mg, 0.6007 mmol) is added under N₂ to a solution of racemic tert-butyl N-[2-[[2-(4-cyclopropylimidazol-1-yl)-1-methyl-ethyl]amino]ethyl]carbamate and racemic tert-butyl N-[2-[[2-(5-cyclopropylimidazol-1-yl)-1-methyl-ethyl]amino]ethyl]carbamate (130 mg, 0.2002 mmol) in THF (5 mL) at room temperature. The mixture is stirred at 60° C. for 2 hours. The reaction mixture is quenched by addition of water. The mixture is extracted with DCM (3×) and the organic extracts are dried over Na₂SO₄, filtered, and concentrated to dryness. The residue is purified by silica gel flash chromatography with 6% MeOH in DCM to give the title compounds as a mixture of regioisomers (37.6 mg, 38.1%) as a yellow oil. ES/MS (m/z): 235 (M+1).

Preparation 13

1-(2-Bromoethyl)-4-cyclopropyl-imidazole

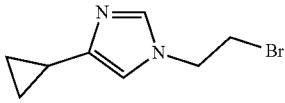

Preparation 14

1-(2-Bromoethyl)-5-cyclopropyl-imidazole

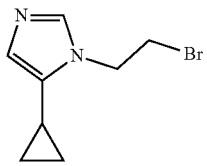 [SMILES: BrCCn1cncc1C1CC1]

NaH (60 mass %) in mineral oil (148 mg, 3.6989 mmol) is added to a solution of 4-cyclopropyl-1H-imidazole (200 mg, 1.8495 mmol) in DMF (2 mL) at 0° C. under a nitrogen atmosphere. The mixture is stirred at 0° C. for 15 minutes. 1,2-Dibromoethane (0.504 mL 5.5484 mmol) is added at 0° C. and the mixture is stirred at room temperature for 4 hours under a nitrogen atmosphere. The reaction is quenched by addition of water. The mixture is extracted with EtOAc (3×). The organic phase is washed with saturated NaCl (3×), dried over Na₂SO₄, filtered, and concentrated to dryness. The residue is purified by silica gel flash chromatography with 3% MeOH in DCM to give the title compound as a mixture of 1-(2-bromoethyl)-4-cyclopropyl-imidazole and 1-(2-bromoethyl)-5-cyclopropyl-imidazole regioisomers (120 mg, 28.7%) as a colorless oil. ES/MS (m/z): 215 (M+1).

Scheme 1

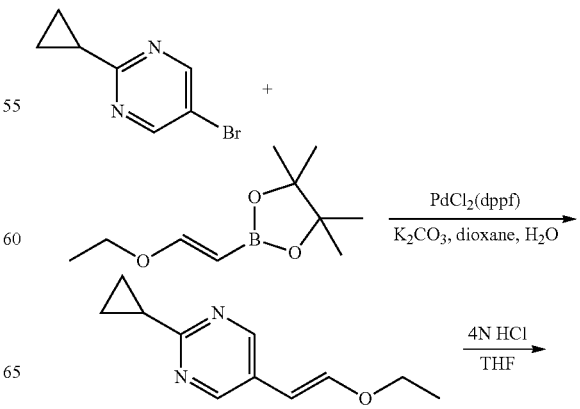

13

-continued

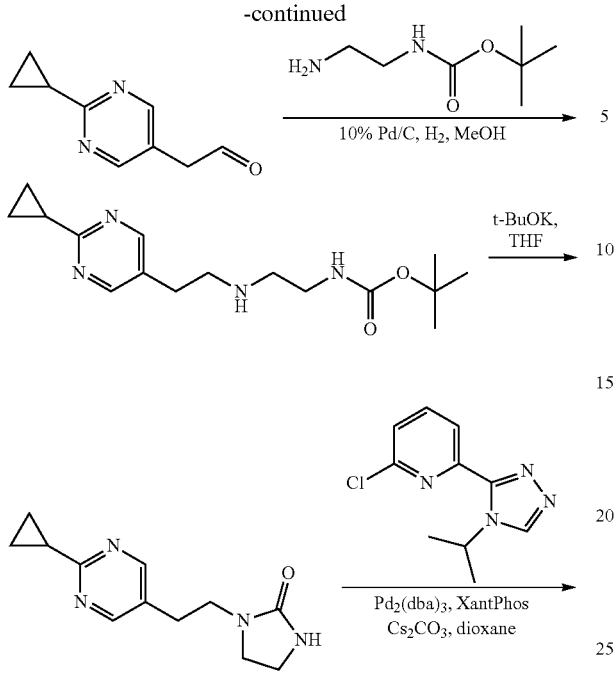

Preparation 15

2-Cyclopropyl-5-[(E)-2-ethoxyvinyl]pyrimidine

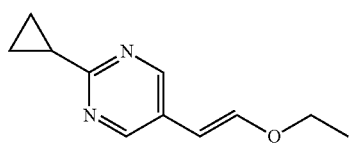

Water (1 mL) is added under N₂ to a solution of 5-bromo-2-cyclopropyl-pyrimidine (200 mg, 0.954 mmol), 2-[(E)-2-ethoxyvinyl]-4,4,5,5-tetramethyl-1,3,2-dioxaborolane (219 mg, 1.05 mmol), 1,1'-bis(diphenylphosphino)ferrocene-palladium(II)dichloride dichloromethane complex (39.8 mg, 0.0477 mmol) and K₂CO₃ (395.8 mg, 2.86 mmol) in 1,4-dioxane (4 mL) at room temperature. The mixture is stirred at 90° C. under N₂ for 18 hours. The mixture is diluted with DCM, dried over Na₂SO₄, filtered, and concentrated to dryness. The residue is purified by silica gel flash chromatography with 13% EtOAc in hexanes to give the title compound (164 mg, 85.8%) as a colorless oil. ES/MS (m/z): 191 (M+1).

14

Preparation 16

2-(2-Cyclopropylpyrimidin-5-yl)acetaldehyde

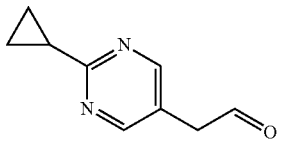 [SMILES: O=CCc1cnc(C2CC2)nc1]

HCl (4 mol/L) in H₂O (2 mL) is added to a solution of 2-cyclopropyl-5-[(E)-2-ethoxyvinyl]pyrimidine (164 mg, 0.819 mmol) in THF (6 mL) at room temperature. The mixture is stirred at 80° C. for 1 hour. The reaction is quenched by addition of saturated NaHCO₃ to adjust the pH to >7. The mixture is extracted with DCM (3×). The organic extracts are dried over Na₂SO₄, filtered, and concentrated to give the crude product (139.8 mg 100.00%) as a yellow oil. The crude product is used without further purification. ES/MS (m/z): 163 (M+1).

Preparation 17 tert-Butyl N-[2-[2-(2-cyclopropylpyrimidin-5-yl)ethylamino]ethyl]carbamate

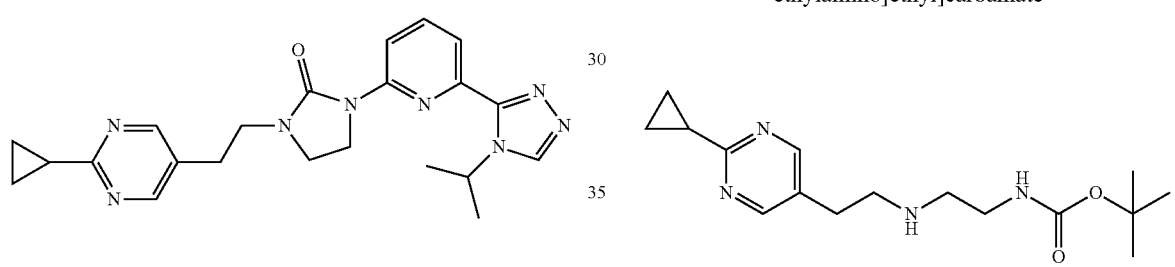

Palladium (10%) on activated carbon (10 mg) is added to a solution of 2-(2-cyclopropylpyrimidin-5-yl)acetaldehyde (139.8 mg, 0.819 mmol) and tert-butyl N-(2-aminoethyl)carbamate (207.1 mg, 1.23 mmol) in MeOH (5 mL) at room temperature. The mixture is stirred at room temperature under 1 atm H₂ for 2 hours. The mixture is filtered through diatomaceous earth and the filtrate is concentrated to give the crude product (264.1 mg, 100.0%) as a colorless oil. ES/MS (m/z): 307 (M+1).

Preparation 18

1-[2-(2-Cyclopropylpyrimidin-5-yl)ethyl]imidazolidin-2-one

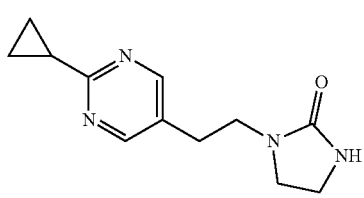 [SMILES: O=C1NCCN1CCc1cnc(C2CC2)nc1]

Potassium tert-butoxide (278.4 mg, 2.46 mmol) is added under N₂ to a solution of tert-butyl N-[2-[2-(2-cyclopropylpyrimidin-5-yl)ethylamino]ethyl]carbamate (264.1 mg, 0.819 mmol) in THF (5 mL) at room temperature. The mixture is stirred at 60° C. under N₂ for 2 hours. The reaction is quenched by the addition of water and extracted with DCM (3×). The organic extracts are dried over Na₂SO₄, filtered, and concentrated to dryness. The residue is purified by silica gel flash chromatography with 4% MeOH in DCM to give the title compound (87 mg, 43.5%) as a white solid. ES/MS (m/z): 233 (M+1).

Preparation 19

6-Aminopyridine-2-carbohydrazide

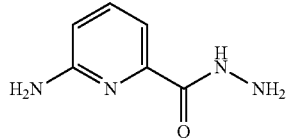

Hydrazine hydrate (118 g, 2310 mmol) is added to a solution of methyl 6-aminopyridine-2-carboxylate (145 g, 953 mmol) in MeOH (1.5 L). The reaction mixture is stirred at 75° C. under a nitrogen atmosphere for 16 hours. After cooling, the resulting precipitate is collected by filtration and is dried under vacuum to give the title compound (130 g, 89.7%) as a white solid. ¹H NMR (400 MHz, d₆-DMSO-) δ 9.15 (br, 1H), 7.51 (t, J=7.8 Hz, 1H), 7.10 (d, J=7.2 Hz, 1H), 6.60 (d, J=8.4 Hz, 1H), 6.07 ((br, 2H), 4.47 ((br, 2H).

Preparation 20

N,6-Bis[(E)-dimethylaminomethyleneamino]pyridine-2-carboxamide

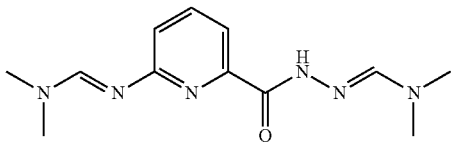

A mixture of 6-aminopyridine-2-carbohydrazide (65.0 g, 427 mmol) in N,N-dimethylformamide dimethyl acetal (600 g, 5040 mmol) is stirred at 95° C. for 1 hour. The reaction is cooled and concentrated under reduced pressure to give a yellow residue. The residue is suspended in EtOAc (300 mL) and stirred for 30 minutes at 25° C. The resulting precipitate is collected by filtration and dried under vacuum to give the title compound (95.0 g, 84.8%) as white solid. ¹H NMR (400 MHz, d₆-DMSO) δ 8.85 (s, 1H), 8.06 (s, 1H), 7.68 (t, J=7.6 Hz, 1H), 7.50-7.45 (m, 1H), 6.91 (d, J=7.6 Hz, 1H), 3.13 (s, 3H), 3.00 (s, 3H), 2.86 (s, 6H)

Preparation 21

6-(4-Isopropyl-1,2,4-triazol-3-yl)pyridin-2-amine

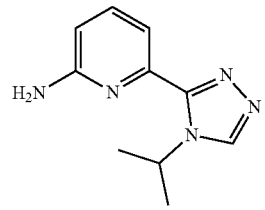

Propan-2-amine (100 g, 1690 mmol) is added to a solution of N,6-bis[(E)-dimethylaminomethyleneamino]pyridine-2-carboxamide (105.0 g, 360 mmol) in ACN (450 mL) and acetic acid (120 mL) in portions maintaining the temperature below 30° C. The resulting mixture is stirred at 110° C. for 60 hours. The reaction mixture is cooled to 25° C., and the solvent is removed under reduced pressure. The residue is dissolved in water (500 mL) and the pH is adjusted to ~10 with aqueous NaOH (1 N). The precipitate is collected by filtration; the filtrate is dissolved in DCM (500 mL), dried over anhydrous Na₂SO₄, and concentrated under reduced pressure to give an off white residue. The residue is suspended in EtOAc (100 mL) and stirred for 15 minutes followed by the slow addition of PE (200 mL). The resulting precipitate is collected by filtration and the filtrate is dried under vacuum to give the title compound (47.0 g, 62.9%) as an off-white solid. ES/MS (m/z): 204.1 (M+1), LCMS: $t_{(R)}$=0.565 min in 0-30% ACN with 0.05% TFA in water over 7.0 minutes (column: Xtimate C18, 2.1*30 mm, 3 μm), ¹H NMR (400 MHz, CD₃OD) δ 8.75 (s, 1H), 7.57 (t, J=8.0 Hz, 1H), 7.20 (d, J=7.2 Hz, 1H), 6.65 (d, J=8.0 Hz, 1H), 5.52 (spt, J=6.8 Hz, 1H), 1.52 (d, J=6.8 Hz, 6H).

Preparation 22

2-Chloro-6-(4-isopropyl-1,2,4-triazol-3-yl)pyridine

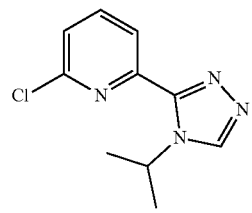

Benzyltriethylammonium chloride (133.2 g, 578.4 mmol) is added to a suspension of 6-(4-isopropyl-1,2,4-triazol-3-yl)pyridin-2-amine (60.0 g, 289.2 mmol) in DCM (1200 mL) at 0° C. tert-Butyl nitrite (124.8 g, 1156.8 mmol) is added by drop-wise addition. The mixture is warmed to 30° C. and stirred for 17 hours. The reaction is quenched by the addition of aq.NaHCO₃ (1200 mL) solution and the product is extracted with DCM (3×1500 mL). The organic extracts are washed with brine, dried over Na₂SO₄ and concentrated in vacuo to give the crude product (64.363 g, 289.2 mmol) as a yellow solid which is purified by silica gel flash chromatography, eluting with a gradient of 0% to 1% MeOH in DCM to give the title compound (36.4 g, 52.6%) as a brown solid. ES/MS m/z (³⁵Cl/³⁷Cl): 223.0/225.0 (M+1), ¹H NMR (400 MHz, CDCl₃) δ 8.37 (s, 1H), 8.26 (dd, J=0.8, 7.8 Hz, 1H), 7.80 (t, J=7.8 Hz, 1H), 7.38 (dd, J=0.8, 7.8 Hz, 1H), 5.67-5.57 (m, 1H), 1.59-1.54 (m, 6H) and ¹³CNMR (100 MHz, CDCl₃) δ=150.63, 150.03, 148.31, 142.49, 139.82, 124.72, 122.38, 49.18, 23.72.

Scheme 2

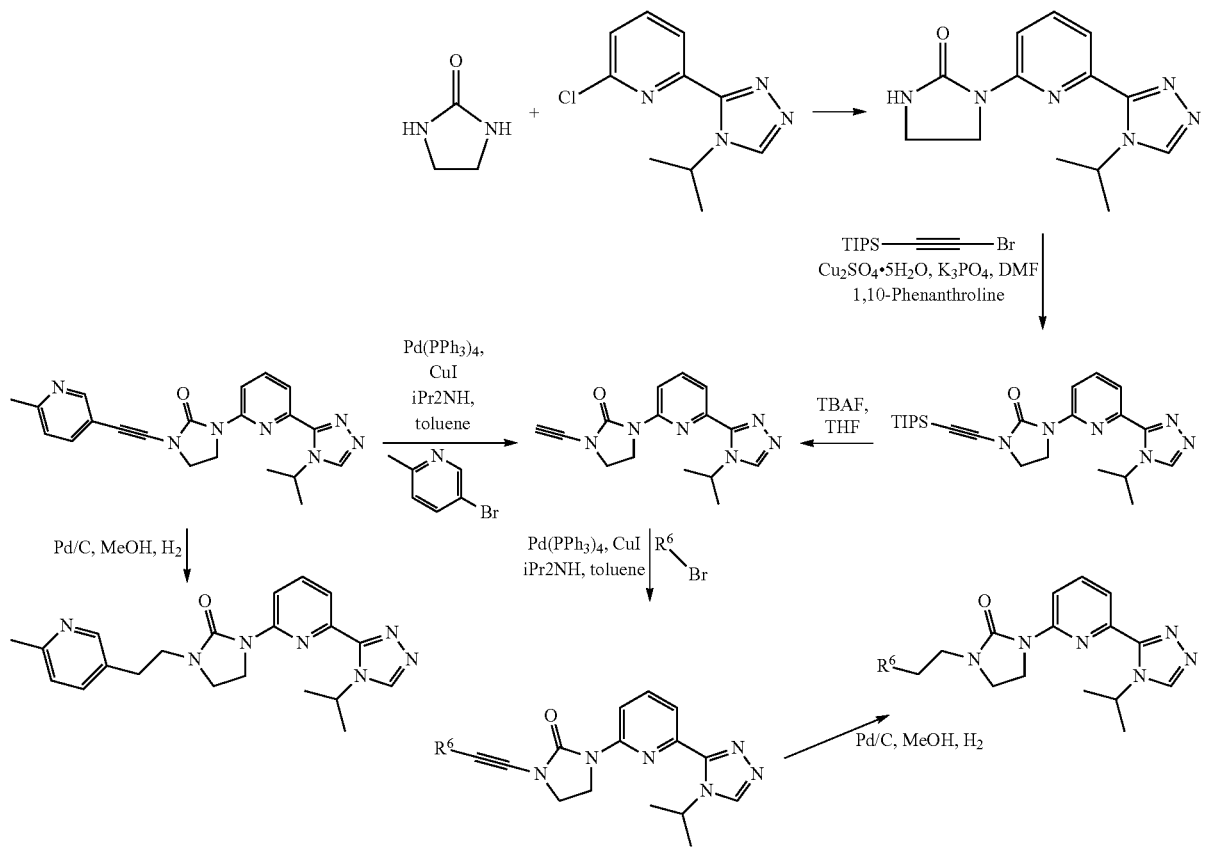

Compounds of this invention wherein R⁶ is selected from the group consisting of

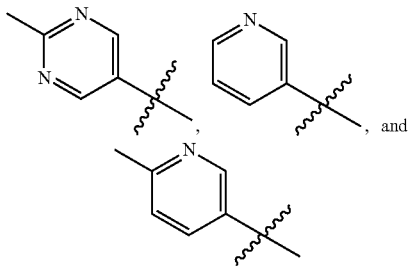, and are prepared generally as illustrated by Scheme 2 using methods substantially as described by the examples.

Preparation 23

1-(6-(4-Isopropyl-4H-1,2,4-triazol-3-yl)pyridin-2-yl)-3-((triisopropylsilyl)ethynyl)imidazolidin-2-one

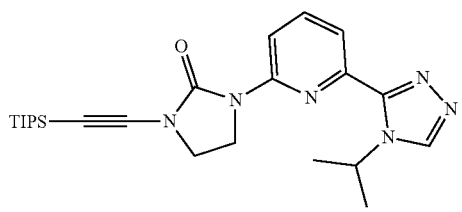

2-Bromoethynyl(triisopropyl)silane (1.5 g, 5.7 mmol), DMF (50 mL) and copper(II) sulfate pentahydrate (0.138 g, 0.551 mmol) are added to a microwave vessel charged with 1-[6-(4-isopropyl-1,2,4-triazol-3-yl)-2-pyridyl]imidazolidin-2-one (1.50 g, 5.51 mmol), tripotassium phosphate (2.34 g, 11.0 mmol) and 1,10-phenanthroline (0.199 g, 1.10 mmol). The mixture is degassed with $N_2$ and heated to 80° C. for 2 hours. The reaction is filtered, concentrated under vacuum, and purified by silica gel flash chromatography, eluting with a gradient of 0% to 5% MeOH in DCM to give the title compound (2.08 g, 75.1%, 90% purity) as a brown solid. ES/MS (m/z): 453 (M+1).

Preparation 24

1-Ethynyl-3-(6-(4-isopropyl-4H-1,2,4-triazol-3-yl)pyridin-2-yl)imidazolidin-2-one

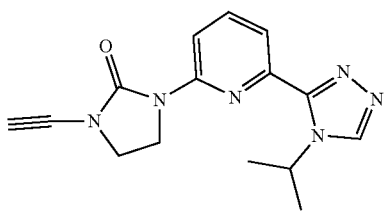 [SMILES: C#CN1CCN(c2cccc(-c3nncn3C(C)C)n2)C1=O]

TBAF (1 M in THF) (4.6 mL, 4.6 mmol) is added to a THF (50 mL) solution of 1-[6-(4-isopropyl-1,2,4-triazol-3- yl)-2-pyridyl]-3-(2-triisopropylsilylethynyl)imidazolidin-2-one (2.08 g, 4.14 mmol, 90 mass %). The mixture is stirred at room temperature for 1 hour. The solvent is removed under vacuum and the residue is purified by silica gel flash chromatography, eluting with a gradient of 0% to 4% MeOH in DCM to give the title compound (897.8 mg, 71.7%, 98% purity) as a white solid. ES/MS (m/z): 297 (M+1).

Preparation 25

1-(6-(4-Isopropyl-4H-1,2,4-triazol-3-yl)pyridin-2-yl)-3-((6-methylpyridin-3-yl)ethynyl)imidazolidin-2-one

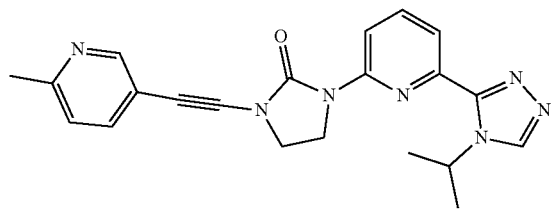 [SMILES: Cc1ccc(C#CN2CCN(c3cccc(-c4nncn4C(C)C)n3)C2=O)cn1]

1-Ethynyl-3-[6-(4-isopropyl-1,2,4-triazol-3-yl)-2-pyridyl]imidazolidin-2-one (100 mg, 0.338 mmol), 5-bromo-2-methyl-pyridine (870.8 mg, 0.5062 mmol), tetrakis(triphenylphosphine)palladium(0) (0.04021 g, 0.03375 mmol), copper iodide (32 mg, 0.017 mmol) are added together and sealed in a microwave vial and degassed with $N_2$ (3×). Diisopropylamine (4 mL) and toluene (2 mL) are added together and the reaction is stirred at room temperature for 1 hour and heated at 80° C. on the microwave reactor for 1 hour. LCMS indicates the formation of the desired product. The reaction is filtered, concentrated under vacuum, and purified by HPLC purification. Conditions: (mobile phase: ACN in water (10 mM $NH_4HCO_3$) 12-27% over 15 min, stop at 21 min.). The title compound is obtained (7.9 mg, 6%, 95% purity) and is isolated as a white solid. ES/MS (m/z): 388 (M+1).

Preparation 26

1-(6-(4-Isopropyl-4H-1,2,4-triazol-3-yl)pyridin-2-yl)-3-((2-methylpyrimidin-5-yl)ethynyl)imidazolidin-2-one

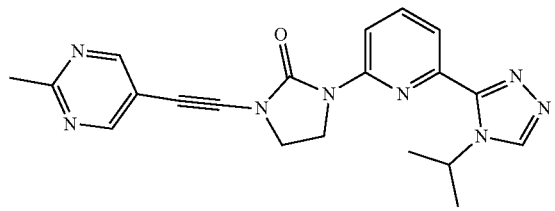 [SMILES: Cc1ncc(C#CN2CCN(c3cccc(-c4nncn4C(C)C)n3)C2=O)cn1]

5-Bromo-2-methyl-pyrimidine (0.1518 g, 0.8775 mmol), 1-ethynyl-3-[6-(4-isopropyl-1,2,4-triazol-3-yl)-2-pyridyl]imidazolidin-2-one (200 mg, 0.6750 mmol), tetrakis(triphenylphosphine)palladium(0) (0.08041 g, 0.06750 mmol) and copper iodide (9.0 mg, 0.047 mmol) are added together and sealed in a microwave vial and degassed with $N_2$ (3×). Diisopropylamine (4 mL) and toluene (2 mL) are added to the mixture and the reaction is heated at 80° C. for 1 hour. The solvents are removed under vacuum and the residue is purified by silica gel flash chromatography, eluting with a gradient of 0% to 5% MeOH in DCM to give the title compound (20 mg, 3.3%, 43% purity) as yellow solid. ES/MS (m/z): 389 (M+1).

Example 1

1-[6-(4-Isopropyl-1,2,4-triazol-3-yl)-2-pyridyl]-3-[2-(3-pyridyl)ethyl]imidazolidin-2-one

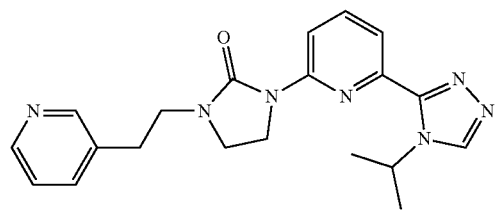 [SMILES: CC(C)n1cnnc1-c1cccc(N2CCN(CCc3cccnc3)C2=O)n1]

Sodium hydride (60 mass %) in mineral oil (19.4 mg, 0.4848 mmol) is added to a solution of 1-[6-(4-isopropyl-1,2,4-triazol-3-yl)-2-pyridyl]imidazolidin-2-one (50 mg, 0.1616 mmol) in DMF (2 mL) at 0° C. The mixture is stirred at 0° C. for 15 minutes. 3-(2-Bromoethyl)pyridine (80 mg, 0.40849 mmol) is added to the mixture and the mixture is stirred at room temperature for 1 hour. The reaction is quenched by addition of water and the mixture is extracted with DCM (3×). The organic extracts are dried over $Na_2SO_4$, filtered, and concentrated to dryness. The residue is purified by prep-HPLC (A: Water (10 mM $NH_4HCO_3$), B: ACN, 16-31% B over 9 minutes) to give the title compound (22 mg, 34.27%) as a white solid. ES/MS (m/z): 378 (M+1), $^1$H NMR (500 MHz, CDCl$_3$) δ 8.62-8.60 (m, 2H), 8.35-8.34 (m, 2H), 7.90 (d, J=7.5 Hz, 1H), 7.78 (t, J=8.0 Hz, 1H), 7.66-7.47 (m, 1H), 7.29-7.26 (m, 1H), 5.60-5.53 (m, 1H), 4.00-3.97 (m, 2H), 3.62 (t, J=7.5 Hz, 2H), 3.45 (t, J=8.0 Hz, 2H), 2.95 (t, J=7.5 Hz, 2H), 1.56 (d, J=7.0 Hz, 6H).

Example 2

1-[(1R)-2-(4-Cyclopropylimidazol-1-yl)-1-methylethyl]-3-[6-(4-isopropyl-1,2,4-triazol-3-yl)-2-pyridyl]imidazolidin-2-one

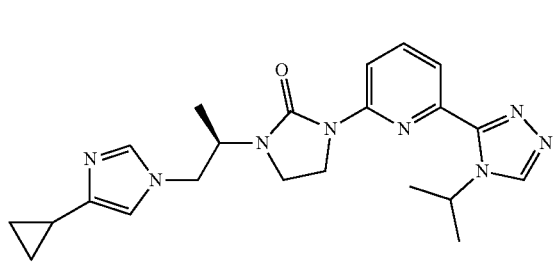 [SMILES: CC(C)n1cnnc1-c1cccc(N2CCN([C@H](C)Cn3cnc(C4CC4)c3)C2=O)n1]

Racemic 1-[2-(4-cyclopropylimidazol-1-yl)-1-methylethyl]imidazolidin-2-one and racemic 1-[2-(5-cyclopropylimidazol-1-yl)-1-methyl-ethyl]imidazolidin-2-one (37.6 mg, 0.0762 mmol), Xantphos PD G3 (76.1 mg, 0.00762 mmol), 4,5-bis(diphenylphosphino)-9,9-dimethylxanthene (XantPhos) (45.5 mg, 0.00762 mmol) and cesium carbonate (74.5 mg, 0.229 mmol) are added together in 1,4-dioxane (2 mL) and the resulting mixture is stirred at 130° C. under microwave conditions for 2 hours. The mixture is diluted with DCM, filtered, and concentrated to dryness. The residue is purified by prep-HPLC (A: Water (0.1% FA), B: ACN (0.1% FA), 7-22% B in 10 min) to give the title compound (27 mg, 77.5%) as a white solid. ES/MS (m/z): 421 (M+1), $^1$H NMR (500 MHz, CDCl$_3$) δ 8.36 (s, 1H), 8.31 (d, J=8.0 Hz, 1H), 7.91 (d, J=7.5 Hz, 1H), 7.80 (t, J=8.0 Hz, 1H), 7.39 (s, 1H), 6.70 (s, 1H), 5.57-5.51 (m, 1H), 4.30-4.23 (m, 1H), 4.13 (dd, J=7.0, 14.0 Hz, 1H), 4.03-3.96 (m, 2H), 3.49-3.32 (m, 1H), 3.23-3.22 (m, 1H), 1.86-1.79 (m, 1H), 1.56 (d, J=7.0 Hz, 6H), 1.32 (d, J=7.0 Hz, 3H), 0.86-0.81 (m, 1H), 0.73-0.68 (m, 1H).

Example 3

1-[2-(4-Cyclopropylimidazol-1-yl)ethyl]-3-[6-(4-isopropyl-1,2,4-triazol-3-yl)-2-pyridyl]imidazolidin-2-one

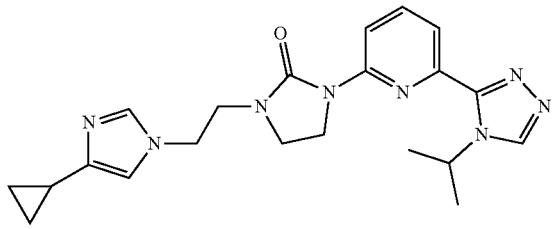 [SMILES: CC(C)n1cnnc1-c1cccc(N2CCN(CCn3cnc(C4CC4)c3)C2=O)n1]

NaH (60 mass %) in mineral oil (39.4 mg, 0.9838 mmol) is added under a nitrogen atmosphere to a solution of 1-[6-(4-isopropyl-1,2,4-triazol-3-yl)-2-pyridyl]imidazolidin-2-one (94 mg, 0.3279 mmol) in DMF (2 mL) at 0° C. The mixture is stirred at 0° C. for 15 minutes and a mixture of 1-(2-bromoethyl)-4-cyclopropyl-imidazole and 1-(2-bromoethyl)-5-cyclopropyl-imidazole (120 mg, 0.2650 mmol) is added at 0° C., and the solution is stirred at room temperature for 1 hour under a nitrogen atmosphere. The reaction is quenched by the addition of water and the mixture is extracted with DCM (3×). The organic extracts are dried over Na$_2$SO$_4$, filtered, and concentrated to dryness. The residue is purified by prep-HPLC: A: H$_2$O (0.1% FA); B: ACN (0.1% FA), gradient: 5-15% B over 15 minutes, stop at 22 minutes; column temperature: room temperature; flow rate: 30 mL/min, t$_{(R)}$=11.2 minutes (UV). The material is concentrated, dissolved in water and lyophilized to give the title compound (32 mg, 22.8%) as a white solid. ES/MS (m/z): 407 (M+1), $^1$H NMR (500 MHz, CDCl$_3$) δ 8.36 (s, 1H), 8.33 (d, J=8.5 Hz, 1H), 7.93 (d, J=7.5 Hz, 1H), 7.81 (t, J=8.0 Hz, 1H), 7.44 (s, 1H), 6.73 (s, 1H), 5.57-5.52 (m, 1H), 4.13 (t, J=6.0 Hz, 2H), 3.95 (t, J=8.0 Hz, 2H), 3.63 (t, J=6.0 Hz, 2H), 3.14 (t, J=8.0 Hz, 2H), 1.87-1.82 (m, 1H), 1.56 (d, J=7.0 Hz, 6H), 0.87-0.84 (m, 2H), 0.74-0.71 (m, 2H).

Example 4

1-[2-(2-Cyclopropylpyrimidin-5-yl)ethyl]-3-[6-(4-isopropyl-1,2,4-triazol-3-yl)-2-pyridyl]imidazolidin-2-one

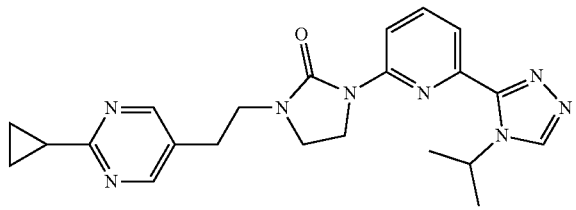 [SMILES: CC(C)n1cnnc1-c1cccc(N2CCN(CCc3cnc(C4CC4)nc3)C2=O)n1]

2-Chloro-6-(4-isopropyl-1,2,4-triazol-3-yl)pyridine (125.1 mg, 0.534 mmol), 1-[2-(2-cyclopropylpyrimidin-5-yl)ethyl]imidazolidin-2-one (87 mg, 0.356 mmol), tris(dibenzylideneacetone)dipalladium(0) (33.6 mg, 0.0356 mmol), XantPhos (42.5 mg, 0.0712 mmol) and Cs$_2$CO$_3$ (347.8 mg, 1.07 mmol) are added together in 1,4-dioxane (2 mL). The mixture is stirred at 130° C. under microwave conditions for 2 hours. The mixture is diluted with DCM, filtered, and concentrated to dryness. The residue is purified by prep-HPLC: A: H$_2$O (0.1% FA); B: ACN (0.1% FA), gradient: 24-39% B over 10 min, stop at 17 min; column temperature: room temperature; flow rate: 30 mL/min, t$_{(R)}$=6.0 minutes (UV). The material is concentrated, dissolved in water, and lyophilized to give the title compound (120 mg, 76.56%) as a white solid. ES/MS (m/z): 419 (M+1), $^1$H NMR (500 MHz, CDCl$_3$) δ 8.48 (s, 2H), 8.36 (s, 1H), 8.33 (d, J=8.5 Hz, 1H), 7.91 (d, J=7.0 Hz, 1H), 7.79 (t, J=8.0 Hz, 1H), 5.59-5.53 (m, 1H), 4.01 (t, J=8.0 Hz, 2H), 3.58 (t, J=7.0 Hz, 2H), 3.48 (t, J=8.0 Hz, 2H), 2.87 (t, J=7.0 Hz, 2H), 2.25-2.20 (m, 1H), 1.56 (d, J=6.5 Hz, 6H), 1.12-1.06 (m, 4H).

Example 5

1-(6-(4-Isopropyl-4H-1,2,4-triazol-3-yl)pyridin-2-yl)imidazolidin-2-one

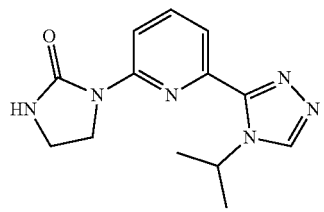 [SMILES: CC(C)n1cnnc1-c1cccc(N2CCNC2=O)n1]

2-Chloro-6-(4-isopropyl-1,2,4-triazol-3-yl)pyridine (100 mg, 0.449 mmol), imidazolidin-2-one (0.116 g, 1.35 mmol), XantPhos Pd G3 (22.4 mg, 0.0225 mmol) and sodium tert-butoxide (89.0 mg, 89.8 mmol) are added together, the mixture is sealed in a microwave vial and degassed with N$_2$ (3×). 1,4-Dioxane (5 mL) is added and the reaction is heated at 140° C. for 3 hours. The reaction mixture is filtered, concentrated, and purified by HPLC; Conditions: (mobile phase: ACN in water (10 mM NH$_4$HCO$_3$) 8-23%, stopped at 9 min. The title compound (1.8 mg, 1.4%, 93% purity) is obtained as a white solid. ES/MS (m/z): 273 (M+1), $^1$H NMR (500 MHz, CD$_3$OD) δ 8.86 (s, 1H), 8.36 (d, J=8.5 Hz 1H), 7.90 (d, J=8.0 Hz, 1H), 7.74 (d, J=7.0 Hz, 1H), 5.63-5.58 (m, 1H), 4.21 (t, J=8.0 Hz, 2H), 3.60 (t, J=8.0 Hz, 2H), 1.61 (d, J=6.5 Hz, 6H).

Example 6

1-[6-(4-Isopropyl-1,2,4-triazol-3-yl)-2-pyridyl]-3-[2-(2-methylpyrimidin-5-yl)ethyl]imidazolidin-2-one

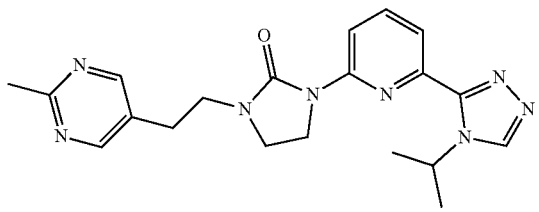 [SMILES: Cc1ncc(CCN2CCN(c3cccc(-c4nncn4C(C)C)n3)C2=O)cn1]

1-[6-(4-Isopropyl-1,2,4-triazol-3-yl)-2-pyridyl]-3-[2-(2-methylpyrimidin-5-yl)ethynyl]imidazolidin-2-one (20 mg, 0.022 mmol, 43 purity %) is added to a MeOH (10 mL) suspension of palladium on carbon (20%) (10 mg). The reaction is degassed with H$_2$ and stirred under an atmosphere of H$_2$ for 1 hour. The reaction is filtered, concentrated under vacuum, and purified by HPLC with the following conditions; (mobile phase: ACN (0.1% FA) in water (0.1% FA) 18-33% over 10 min, stop at 17 minutes. The title compound (2 mg, 21.86%, 95% purity) is obtained as a white solid. ES/MS (m/z): 393 (M+1), $^1$H NMR (500 MHz, CD$_3$OD) δ 8.87 (s, 1H), 8.68 (s, 2H), 8.29 (d, J=7.0 Hz, 1H), 7.89 (t, J=7.5 Hz, 1H), 7.73 (d, J=6.5 Hz, 1H), 5.62-5.57 (m, 1H), 4.11 (t, J=8.0 Hz, 2H), 3.67-3.61 (m, 4H), 2.98 (t, J=7.0 Hz, 2H), 2.67 (s, 3H), 1.61 (d, J=6.5 Hz, 6H).

Example 7

1-[6-(4-Isopropyl-1,2,4-triazol-3-yl)-2-pyridyl]-3-[2-(6-methyl-3-pyridyl)ethyl]imidazolidin-2-one

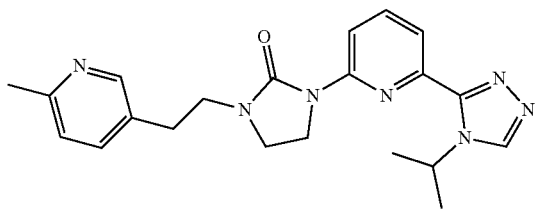 [SMILES: Cc1ccc(CCN2CCN(c3cccc(-c4nncn4C(C)C)n3)C2=O)cn1]

1-[6-(4-isopropyl-1,2,4-triazol-3-yl)-2-pyridyl]-3-[2-(6-methyl-3-pyridyl)ethynyl]imidazolidin-2-one (7.9 mg, 0.019 mmol) is added to a MeOH (10 mL) suspension of palladium on carbon (20%) (10 mg). The reaction is degassed with H$_2$ and stirred under an atmosphere of H$_2$ for 1 hour. The reaction is filtered, concentrated, and purified by HPLC with the following conditions: (mobile phase: ACN in water (10 mM NH$_4$HCO$_3$) 18-28% over 10 minutes, stop at 15 minutes. The title compound (2 mg, 92%, 95% purity) is isolated as a white solid. ES/MS (m/z): 392 (M+1), $^1$H NMR (500 MHz, CD$_3$OD) δ 8.85 (s, 1H), 8.36 (s, 1H), 8.32-8.30 (d, J=8.5 Hz, 1H), 7.88 (dd, J=7.6, 8.6 Hz, 1H), 7.74-7.71 (m, 2H), 7.28 (d, J=8.0 Hz, 1H), 5.60-5.51 (m, 1H), 4.08 (t, J=8.0 Hz, 2H), 3.61-3.58 (m, 4H), 2.96 (t, J=7.0 Hz, 2H), 2.51 (s, 3H), 1.60 (d, J=7.0 Hz, 6H).

Biological Assays

ASK1 Inhibitor Effect Determined by ASK1 Enzymatic Assay

The purpose of this assay is to determine the effect of ASK1 inhibitors on the production of ADP by ASK1. The recombinant human ASK1 (hASK1) catalytic domain tagged with Glutathione S-transferase is used, and histidine-tagged full-length human MAP kinase kinase 6 (MKK6) and ATP are the substrate and cofactor, respectively.

The assay is done using an ADP-Glo™ Kinase Assay Kit (Promega, Catalog #V9102) according to the manufacturer's protocol with the following modifications. Briefly, hASK1 (0.25 nM) and MKK6 (300 nM) in a buffer (10 mM MOPS pH 7.0; 10 mM Mg-Acetate; 1 mM DTT; 0.025% NP-40; 0.05% BSA; 1.5% glycerol) are incubated with ASK1 inhibitors at varying concentrations ranging from 10.00 uM to 0.17 nM for 15 minutes, followed by incubation with ATP (100 uM) for 30 minutes at room temperature. ADP-Glo™ Reagent is added to terminate the kinase reaction and deplete the remaining ATP. The Kinase Detection Reagent is then added to convert ADP to ATP. The newly synthesized ATP is measured using a luciferase/luciferin reaction, and the luminescence determined by Envision (PerkinElmer). The luminescence intensities are analyzed by GeneData, and fit to a 4 parameter dose response-inhibitor logistics curve to determine IC$_{50}$ values, using the effects of 5-(4-cyclopropyl-1H-imidazol-1-yl)-2-fluoro-4-methyl-N-{6-[4-(propan-2-yl)-4H-1,2,4-triazol-3-yl]pyridin-2-yl}benzamide as a standard and DMSO vehicle for 100% and 0% inhibition, respectively.

The Examples are tested essentially as described above and exhibit IC$_{50}$ values as shown in Table 1 below.

TABLE 1

| Example # | hASK1 IC$_{50}$ (nM) | Efficacy (%) |
| --- | --- | --- |
| 1 | 36.0 ± 6.25, n = 2 | 100 |
| 2 | 14.0 ± 2.61, n = 2 | 100 |
| 3 | 10.8 ± 2.01, n = 4 | 100 |
| 4 | 13.7 ± 6.57, n = 4 | 100 |
| 5 | 64.4 ± 58.5, n = 4 | 100 |
| 6 | 88.3 ± 21.8, n = 2 | 100 |
| 7 | 16.6 ± 3.16, n = 4 | 100 |

Mean±Standard Deviation

These results indicate that the compounds of the Examples inhibit ASK1 enzymatic activity as shown in Table 1.

ASK1 Inhibitor Effect Determined by ASK1 Autophosphorylation (Thr838) Assay

The purpose of this assay is to determine the effect of ASK1 inhibitors on H$_2$O$_2$-stimulated ASK1 autophosphorylation at Thr838 in HEK293 cells overexpressing human ASK1.

HEK293 cells overexpressing human influenza hemagglutinin- (HA-) tagged full length human ASK1 are maintained in DMEM supplemented with 10% FBS at 37° C. and 5% CO$_2$. For the assay, the cells are plated in matrigel-coated 96-well plates (25,000 cells/well) and incubated overnight. The cells are treated with ASK1 inhibitors at varying concentrations ranging from 10.00 μM to 0.17 nM for 1 hour, followed by stimulation with 1 mM H$_2$O$_2$ for 10 minutes. The cells are then lysed with Homogeneous Time-Resolved Fluorescence (HTRF®) lysis buffer (Cisbio, Catalog #64KL1FDF) containing phosphatase inhibitors (ThermoFisher, Catalog #78430). pASK1 is quantified by HTRF®, using an anti-HA and anti-pASK1 (Thr838) antibody pair customized by Cisbio, on Envision (PerkinElmer) with emission and excitation wavelengths of 620 and 665 nm, respectively. The ratios of fluorescence intensities at 665 nm and 620 nm are analyzed by GeneData, and fit to a 4 parameter dose response-inhibitor logistics curve to determine $IC_{50}$ values, using the effects of 5-(4-cyclopropyl-1H-imidazol-1-yl)-2-fluoro-4-methyl-N-{6-[4-(propan-2-yl)-4H-1,2,4-triazol-3-yl]pyridin-2-yl}benzamide as a standard and DMSO vehicle as 100% and 0% inhibition, respectively.

The compounds are tested essentially as described above and exhibit $IC_{50}$ values as shown in Table 2 below.

TABLE 2

| Example # | HEK pASK1 $IC_{50}$ (nM) | Efficacy (%) |
|---|---|---|
| 1 | 1400 | 80.5 |
| 2 | 886 ± 65.4, n = 2 | 96.0 |
| 3 | 1130 ± 300, n = 3 | 101 |
| 4 | 735 | 107 |
| 5 | 3770 | 100 |
| 7 | 520 | 100 |

Mean±Standard Deviation

These results indicate that the compounds of the Examples above inhibit $H_2O_2$-stimulated ASK1 autophosphorylation at Thr838 in HEK293 cells as shown in Table 2 above.

We claim:
1. A compound of the formula

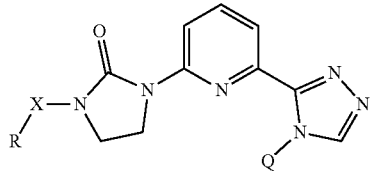

wherein
X is selected from the group consisting of —(CH$_2$)$_2$— and —CH$_2$—CH(CH$_3$)—;
Q is selected from the group consisting of —C(CH$_3$)$_2$ and

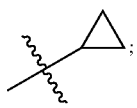

R is selected from the group consisting of

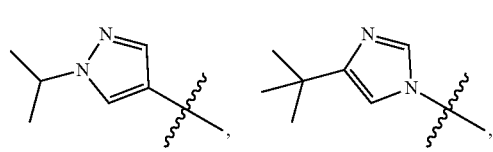

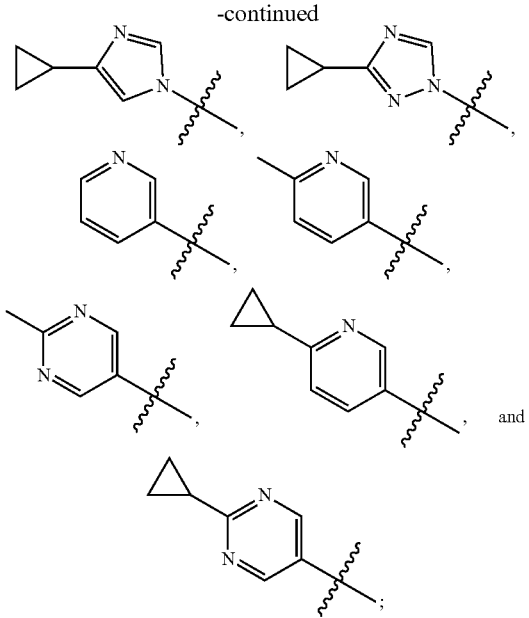

or
a pharmaceutically acceptable salt thereof.
2. A compound as claimed by claim 1, wherein Q is —C(CH$_3$)$_2$.
3. A compound as claimed by claim 2 wherein R is selected from the group consisting of

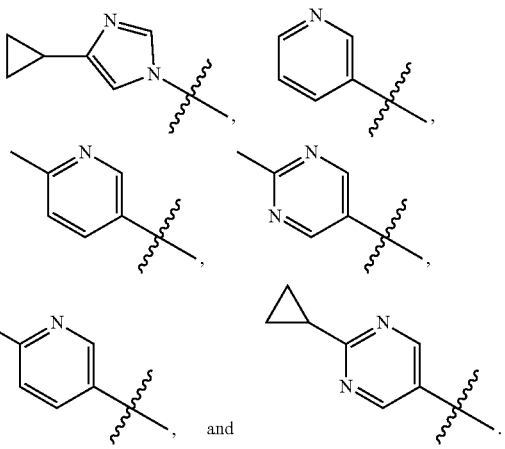

4. A compound as claimed by claim 3 wherein X is —(CH$_2$)$_2$—.
5. A compound as claimed by claim 3 wherein X is —CH$_2$—CH(CH$_3$)—.
6. A compound as claimed by claim 3 wherein R is

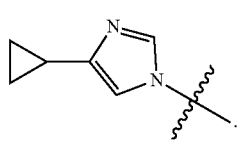 [SMILES: *n1cnc(C2CC2)c1]

7. A compound as claimed by claim 3 wherein R is

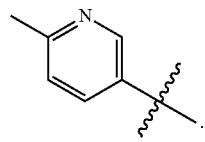 [SMILES: *c1ccc(C)nc1]

8. A compound as claimed by claim 1 wherein the compound is 1-[2-(4-cyclopropylimidazol-1-yl)ethyl]-3-[6-(4-isopropyl-1,2,4-triazol-3-yl)-2-pyridyl]imidazolidin-2-one, or a pharmaceutically acceptable salt thereof.

9. A compound as claimed by claim 1 wherein the compound is 1-[(1 R)-2-(4-cyclopropylimidazol-1-yl)-1-methyl-ethyl]-3-[6-(4-isopropyl-1,2,4-triazol-3-yl)-2-pyridyl]imidazolidin-2-one; or a pharmaceutically acceptable salt thereof.

10. A pharmaceutical formulation comprising a compound as claimed by claim 1, or a pharmaceutically acceptable salt thereof, and at least one selected from the group consisting of a pharmaceutically acceptable carrier, diluent, and excipient.

11. A method for treating nonalcoholic steatohepatitis (NASH), comprising administering to a mammal in need thereof, an effective amount of a compound as claimed by claim 1, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 11,124,496 B2 | |
| APPLICATION NO. | : 16/644746 | |
| DATED | : September 21, 2021 | |
| INVENTOR(S) | : Liu et al. | |

It is certified that error appears in the above-identified patent and that said Letters Patent is hereby corrected as shown below:

In the Claims

Column 27, Line 15, In Claim 9, delete "1-[(1 R)" and insert -- 1-[(1R) --, therefor.

Signed and Sealed this
Third Day of May, 2022

*Katherine Kelly Vidal*

Katherine Kelly Vidal
*Director of the United States Patent and Trademark Office*